United States Patent [19]

Loev et al.

[11] Patent Number: 4,472,430
[45] Date of Patent: Sep. 18, 1984

[54] ALPHA-ALKYL POLYOLEFINIC CARBOXYLIC ACIDS AND DERIVATIVES THEREOF USEFUL IN THE TREATMENT OF PSORIASIS

[75] Inventors: Bernard Loev, Scarsdale; Wan-kit Chan, Yorktown Heights; Howard Jones, Ossining, all of N.Y.

[73] Assignee: USV Pharmaceutical Corporation, Tarrytown, N.Y.

[21] Appl. No.: 392,837

[22] Filed: Jun. 28, 1982

[51] Int. Cl.$^3$ .................. A61K 31/215; A61K 31/20; C07C 57/03; C07C 69/587
[52] U.S. Cl. .................................. 424/312; 424/308; 424/318; 424/320; 424/324; 424/DIG. 4; 260/410.9 R; 260/413; 260/404
[58] Field of Search .................... 260/410.9 R, 413 L; 424/318, 320, 324, 305, 308, 312; 564/191

[56] References Cited

U.S. PATENT DOCUMENTS 3,934,028  1/1976  Lee ..................................... 424/318
4,021,573  5/1977  Lee ..................................... 424/318

OTHER PUBLICATIONS

Haeck, H. H. et al., *Rec. Trav. Chim.*, 85 (1966) 334–338.
Kligman, Lorraine et al., *J. Investigative Dermatology*, vol. 73 (1979) pp. 354–358.
Marcelo, Cynthia L. et al., *J. Cell Biology*, vol. 79, (1978) pp. 356–370.
Ballag, Werner, *Chemical Abstracts*, vol. 75 (1971) #67486e.
Mills, O. H. et al., Assay of Comedolytic Agents in the Rabbit Ear, Animal Models in Dermatology; Relevance to Human Dermatopharmacology and Dermatology, Maibach, H. J., ed., New York, Churchill–Livingston, Publ. (1975) pp. 176–183.

*Primary Examiner*—Natalie Trousof
*Assistant Examiner*—L. Hendriksen

[57] ABSTRACT

Polyolefinic compounds, useful in the treatment of psoriasis, are disclosed. The compounds are represented by the general formula

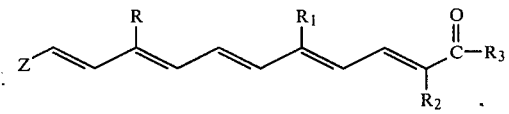

in which R and $R_1$ are each hydrogen or an alkyl group of from 1 to 5 carbon atoms; $R_2$ is an alkyl group of from 1 to 5 carbon atoms; $R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl or trifluoromethyl groups or halogen atoms or combinations thereof and the pharmaceutically-acceptable salts thereof.

The foregoing compounds have been found to be effective in the treatment of psoriasis.

9 Claims, No Drawings

ALPHA-ALKYL POLYOLEFINIC CARBOXYLIC ACIDS AND DERIVATIVES THEREOF USEFUL IN THE TREATMENT OF PSORIASIS

BACKGROUND OF THE INVENTION

The present invention relates to novel alpha-alkyl polyolefinic carboxylic acids derived from such polyolefinic intermediates as retinal (3,7-dimethyl-9-(2,6,6-trimethyl-1-cyclohexen-1-yl)-2,4,6,8-nonatetraenal; vitamin A aldehyde) which possesses the structure

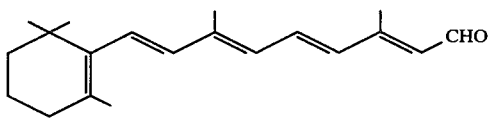

A synthesis of retinal from beta-ionone and propargyl halide is described in U.S. Pat. No. 3,060,229.

A number of alpha-substituted polyolefinic carboxylic aldehydes, acids and esters are described in the scientific literature. Japanese Patent 10,124 (1964); C.A. 62, 2798 g (1965) describes 2,7-dimethyl-9-(2,6,6-trimethyl-1-cyclohexen-1-yl)-2,4,6,8-nonatetraenoic acid and 2,7,11-trimethyl-13-(2,6,6-trimethyl-1-cyclohexen-1-yl)-2,4,6,8,10,12-tridecahexanenoic acid; Machleidt, et al., *Justus Liebigs Ann. Chem.*, 679,20 (1964) describes α-fluoropolyolefinic acids and esters; Chan, et al., *J.A.C.S.* 96, 3642 (1974) describe polyolefinic carboxaldehydes; Haeck, et al., Recuil 85 (1966) pp. 334–338 describe 5,9-dimethyl-11-(2,6,6-trimethyl-1-cyclohexen-1-yl)-2,4,6,8,10-undecapentaenoic acid and corresponding 2,4,6,8,10,12-tridecahexanenoic acids as well as the corresponding α-cyano and α-carboxy substituted compounds. Buchta, et al., *Naturwissenschaften* 46, 74 (1959) describe methyl-2-methyl-7-phenyl-2,4,6-heptatrienoate.

SUMMARY OF THE INVENTION

The present invention is directed to novel alpha-alkyl, polyolefinic carboxylic acids and derivatives thereof of the general formula

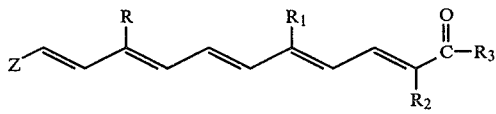

in which R and $R_1$ are each hydrogen or an alkyl group of from 1 to 5 carbon atoms; $R_2$ is an alkyl group of from 1 to 5 carbon atoms; $R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group, or a phenyl group substituted with from 0 to 4 hydroxy, alkoxy, alkyl or trifluoromethyl groups or halogen atoms or combinations thereof; and the pharmaceutically-acceptable salts thereof. The invention includes compounds wherein the double bonds are in the cis or trans configuration.

The foregoing compounds have been found to be effective in the treatment of psoriasis, acne, and cellular and humoral immunodeficiancy.

DESCRIPTION OF THE PREFERRED EMBODIMENTS

A preferred group of compounds within the aforesaid general formula are those in which $R_1$ is methyl, $R_3$ is hydroxyl or alkoxy of from 1 to 5 carbon atoms and Z is a cycloalkenyl group substituted with from 0 to 3 alkyl groups, or a phenyl group substituted with from 1 to 4 alkoxy or alkyl groups containing up to 5 carbon atoms or combinations of the foregoing, including those compounds in which one or more of the double bonds are in the cis configuration. Within this preferred group of compounds, still more preferred are compounds in which Z is the group 2,6,6-trimethyl-1-cyclohexen-1-yl.

The compounds of this invention can be prepared from known polyolefinic materials, e.g., retinal, employing known synthetic procedures of from analogous polyolefinic compounds which can be prepared in accordance with methods known by those skilled in the art.

For example, employing retinal as starting compound, condensation through the aldehyde group with the active methylene group of suitable acids or acid derivatives of the formula:

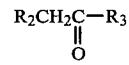

will result in the corresponding undecapentaenoic acid derivative. Activating substituents on the alpha carbon atom of the said compounds, e.g., trialkylphosphono derivatives, facilitate the condensation reaction.

The condensation reaction is usually carried out by reacting the selected starting materials in a suitable solvent preferably in the presence of a strong base such as sodium hydride, sodamide, sodium ethoxide and similar alkali metal compounds. The reaction is usually exothermic and is consequently cooled to control the rate of reaction. After the initial reaction has subsided, the reaction mixture is heated at reflux to assure completeness of reaction.

A variety of reaction solvents can be employed including dioxane, tetrahydrofuran (THF), dimethylformamide, dimethylacetamide and similar water-miscible organic solvents. The solvents employed are preferably anhydrous, particularly when the alkali metal bases are used, to avoid secondary reactions.

The present new compounds can also be prepared from corresponding compounds containing only alpha hydrogen by alkylation using alkylating agents such as dialkyl sulfates, e.g., dimethyl and diethyl sulfate and alkyl halides, e.g., propyl bromide and ethyl bromide, in the presence of alkali metals or alkali metal compounds which react with alpha halogen, e.g., sodium hydride, lithium, potassium, sodamide and alkali metal alkoxides such as sodium or potassium ethoxide.

The compounds of this invention are also prepared by partial reduction of corresponding compounds containing acetylenic in lieu of ethylenic bonds. In addition, the dehydrohalogenation of corresponding alpha-halo acid with no ethylenic bond between alpha and beta carbon atoms also leads to the present compounds.

A further preparative method involves condensation of appropriate side chains with the appropriately substituted cyclohexanone with, for example, an omegahaloundecapentaenoate, preferably in the form of the corresponding Grignard reagent, followed by hydrolysis of the product to form the α-substituted cyclohexanol and then dehydration to the cyclohexenyl compound. The side chain, i.e., the eleven carbon side chain can be formed piecemeal by suitable condensation employing the half aldehyde of a dicarboxylic acid of suitable carbon content to condense with a side chain of suitable carbon content with groups suitable to react with the aldehyde functional group.

A still further process can be used involving oxidation of derivatives of the desired undecapentaenoic acid with mild oxidants such as hypochlorite, e.g., sodium hypochlorite. The oxidants selected should preferably avoid secondary reactions with the remainder of the substrate molecule, or the oxidation should be carried out under controlled conditions to avoid appreciable secondary reactions, as by conducting oxidation with hypochlorite solution at or below about 10° C. and preferably between 0° and 5° C. For example, a compound of the formula

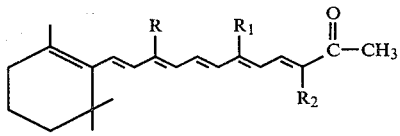

on oxidation with hypochlorite yields the corresponding acid of formula I herein. These new compounds can also be prepared by dehydration of corresponding α or β hydroxy acids or esters to form an alpha-beta ethylenic bond. The beta hydroxy acids or esters can be formed by condensation of an alpha-halo-carboxylic acid (or ester) with an aldehyde of two carbons less than the desired side chain in the presence of zinc (the Reformatsky Reaction).

The present compounds can also be prepared by oxidation of the corresponding aldehyde and alcohol of the same carbon content using oxidizing agents known for such reaction, e.g., hypochloride, as previously described.

EXAMPLE 1

Ethyl 2,5,9-Trimethyl-11-(2,6,6-trimethyl-1-cyclohexen-1-yl)-2,4,6,8,10-undecapentaenoate

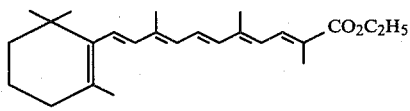

Sodium hydride (4.03 g, 50% dispersion in mineral oil) was washed with dry pentane three times and suspended in 50 ml of anhydrous THF under nitrogen. The stirred mixture was cooled in an ice-water bath and 20.6 g of triethyl 2-phosphonopropionate was added dropwise. The resulting mixture was stirred for additional two hours while allowing the reaction mixture to warm up slowly to room temperature. The mixture was then cooled in an ice-water bath and a solution of retinal (16 g) in 50 ml of anhydrous THF was added dropwise. The resulting dark red mixture was stirred for four hours at room temperature; 700 ml of cold water was added and the mixture was extracted with three 200-ml portions of ether. The combined ethereal solution was washed with 100 ml of water and dried over sodium sulfate. Removal of solvent gave the crude ester (20 g, 97%) as a dark red oily substance. This material was used for the preparation of the free acid of Example 2 without further purification.

EXAMPLE 2

2,5,9-Trimethyl-11-(2,6,6-trimethyl-1-cyclohexen-1-yl)-2,4,6,8,10-Undecapentaenoic Acid

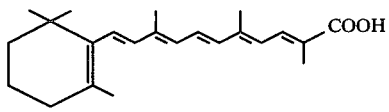

The crude ethyl ester (20 g) from Example 1 was dissolved in 50 ml of ethanol and a solution of potassium hydroxide (5.12 g) in 45 ml of ethanol and 5 ml of water was added dropwise with stirring under nitrogen. The resulting mixture was stirred for 12 hours at room temperature. The reaction mixture was partially concentrated under reduced pressure and then mixed with 500 ml of water. The resulting mixture was extracted with three 150 ml portions of ether. The ethereal layer was discarded, the aqueous layer was acidified to pH 3 with 10N aqueous hydrochloric acid. The resulting product was extracted into ether. The ethereal solution was washed with water and dried over sodium sulfate. Concentration and filtration of this solution afforded the desired product as orange-red powders. Recrystallization in acetone/ethanol gave 9.3 g (50.6%) of pure product, mp 197°–199° C., UV spectrum (methanol) max 380 nm.

In like manner to the procedures described in Examples 1 and 2, the following compounds were prepared:

Ethyl 2-ethyl-5,9-dimethyl-11-(2,6,6-trimethyl-1-cyclohexen-1-yl)-2,4,6,8,10-undecapentaenoate (an oil);

Ethyl-2-propyl-5,9-dimethyl-11-(2,6,6-trimethyl-1-cyclohexen-1-yl)-2,4,6,8,10-undecapentaenoate (an oil);

2-Ethyl-5,9-dimethyl-11-(2,6,6-trimethyl-1-cyclohexen-1-yl)-2,4,6,8,10-undecapentaenoic acid (m.p. 162°–165° C.);

2-Propyl-5,9-dimethyl-11-(2,6,6-trimethyl-1-cyclohexen-1-yl)-2,4,6,8,10-undecapentaenoic acid (m.p. 172°–175° C.).

The compounds of this invention are active against various skin disorders, such as acne and psoriasis, when tested according to models considered to be predictive of the clinical condition in humans. The models used were the rhino mouse procedure (Kligman, et al., *J. Investigative Dermatology* 73, 354 (1979)), the rabbit comedolytic procedure (Mills OH, Kligman AM: Assay of Comedolytic Agents in the Rabbit Ear, Animal Models in Dermatology; Relevance to Human Dermatopharmacology and Dermatotoxicology, edited by H. I. Maibach, New York Churchill-Livingston, 1975, pp. 176–183) and the mouse epidermal cell culture procedure (Marcelo, et al., *J. Cell Biol.*, 79, 356 (1978)). Testing was done comparatively against standard retinoids known to be effective in these disorders and against a known α-methyl retinoid (2,7-dimethyl-9-(2,6,6-trimethyl-1-cyclohexene-1-yl-2,4,6,8-nonatetraenoic acid, referred to as DTCNA).

Activity equal to or greater than the standards and the known compound was shown by 2,5,9-trimethyl-11-(2,6,6-trimethyl-1-cyclohexene-1-yl)-2,4,6,8,10- undecapentaenoic acid (TTCUA). Thus, in the rabbit ear model at a concentration of 0.05%, it was equal to trans retinoic acid (TRA) in ability to reduce comedone size. In the rhino mouse model at the same concentration, it was equal to TRA in ability to reduce significantly the size of utriculi (pseudocomedones) and the amount of horny impaction in the utriculi. The skin of these mice showed moderate epidermal hyperplasia and significantly less wrinkling than the untreated control animals.

In the mouse epidermal cell culture at a concentration of 12 ug/ml, it reduced cell proliferation, as measured by inhibition of the uptake of tritiated thymidine into DNA. Table I shows percentage uptake relative to vehicle control (100%).

TABLE I

| Day of Culture Exposure to Drug | TRA | CRA (13-cis retinoic acid) | TTCUA | DTCNA |
|---|---|---|---|---|
| 3 | 77 | 47 | 31 | 53 |
| 5 | 53 | 75 | 15 | 61 |
| 10 | 36 | 64 | 21 | 60 |

Percentage uptake with TTCUA is seen to be up to five fold less at all time points in comparison to both standards. Known compound DTCNA in contrast is seen to give about the same percentage uptake as the standard drugs at all three time points. Likewise TTCUA showed high anti-differentiation activity at 12 ug/ml in the mouse epidermal cell culture, as shown in Table II.

TABLE II

| Day of Culture Exposure to Drug | Vehicle Control | TRA | CRA (13-cis retinoic acid) | TTCUA | DTCNA |
|---|---|---|---|---|---|
| 3 | 3/6 | 3/5 | 2/7 | 2/6 | 3/6 |
| 6 | 3/5 | 3/5 | 2/7 | 0.5/8.5 | 2/6 |
| 10 | 7.5/2 | 2/6 | 2/6.5 | 1/7.5 | 2/5 |

The ratios in the table represent scoring of two measured parameters, culture staining by the Kreyberg technique (maximum differentiation 10) and nuclei enumeration (maximum differentiation 0). Thus the highest possible anti-differentiative activity would be given by the ratio 0/10. TTCUA is seen to be more active in both parameters than the two standards whereas the known compounds is about the same as the standards.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic. When applied topically, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other similar agents and the dosage level is of the same order of magnitude as is generally employed in the treatment of psoriasis and related conditions.

A convenient form for administration of the present new compounds are salts of those compounds in which $R_3$ is OH, particularly salts with alkali metals such as sodium and potassium, the ammonium salt and salts with organic amines, particularly those commonly employed in pharmaceutical formulations. The salts, of course, should be pharmaceutically-acceptable, that is the salt formation does not appreciably increase the toxicity of the therapeutic agent nor cause a toxic reaction in the host.

What is claimed is:

1. Ethyl 2-ethyl-5,9-dimethyl-11-(2,6,6-trimethyl-1-cyclohexen-1-yl)-2,4,6,8,10-undecapentaenoate.

2. Ethyl 2-propyl-5,9-dimethyl-11-(2,6,6-trimethyl-1-cyclohexen-1-yl)-2,4,6,8,10-undecapentaenoate.

3. 2-Ethyl-5,9-dimethyl-11-(2,6,6-trimethyl-1-cyclohexen-1-yl)-2,4,6,8,10-undecapentaenoic acid and pharmaceutically acceptable salts thereof.

4. 2-Propyl-5,9-dimethyl-11-(2,6,6-trimethyl-1-cyclohexen-1-yl)-2,4,6,8,10-undecapentaenoic acid and pharmaceutically acceptable salts thereof.

5. A therapeutic composition for the treatment of psoriasis in a human host which comprises, in combination with at least one pharmaceutically-acceptable extender, an effective amount for the treatment of psoriasis of ethyl 2-ethyl-5,9-dimethyl-11-(2,6,6-trimethyl-1-cyclohexen-1-yl)-2,4,6,8,10-undecapentaenoate.

6. A therapeutic composition for the treatment of psoriasis in a human host which comprises, in combination with at least one pharmaceutically-acceptable extender, an effective amount for the treatment of psoriasis of ethyl 2-propyl-5,9-dimethyl-11-(2,6,6-trimethyl-1-cyclohexen-1-yl)-2,4,6,8,10-undecapentaenoate.

7. A therapeutic composition for the treatment of psoriasis in a human host which comprises, in combination with at least one pharmaceutically-acceptable extender, an effective amount for the treatment of psoriasis of 2-ethyl-5,9-dimethyl-11-(2,6,6-trimethyl-1-cyclohexen-1-yl)-2,4,6,8,10-undecapentaenoic acid or pharmaceutically-acceptable salts thereof.

8. A therapeutic composition for the treatment of psoriasis in a human host which comprises, in combination with at least one pharmaceutically acceptable extender, an effective amount for the treatment of psoriasis of 2-propyl-5,9-dimethyl-11-(2,6,6-trimethyl-1-cyclohexen-1-yl)-2,4,6,8,10-undecapentaenoic acid or pharmaceutically acceptable salts thereof.

9. A method for treating psoriasis in a human host which comprises administering to said host a therapeutically effective amount for the treatment of psoriasis of a polyolefinic compound selected from the group consisting of: ethyl 2-ethyl-5,9-dimethyl-11-(2,6,6-trimethyl-1-cyclohexen-1-yl)-2,4,6,8,10-undecapentaenoate; ethyl 2-propyl-5,9-dimethyl-11-(2,6,6-trimethyl-1-cyclohexen-1-yl)-2,4,6,8,10-undecapentaenoate; 2-ethyl-5,9-dimethyl-11-(2,6,6-trimethyl-1-cyclohexen-1-yl)-2,4,6,8,10-undecapentanoic acid or pharmaceutically-acceptable salts thereof; and 2-propyl-5,9-dimethyl-11-(2,6,6-trimethyl-1-cyclohexen-1-yl)-2,4,6,8,10-undecapentaenoic acid or pharmaceutically-acceptable salts thereof.

* * * * *